United States Patent [19]
Baldwin

[11] Patent Number: 4,930,894
[45] Date of Patent: Jun. 5, 1990

[54] MINIMUM DEADPATH INTERFEROMETER AND DILATOMETER

[75] Inventor: Richard R. Baldwin, Saratoga, Calif.

[73] Assignee: Hewlett-Packard Company, Palo Alto, Calif.

[21] Appl. No.: 220,899

[22] Filed: Jul. 14, 1988

Related U.S. Application Data

[60] Continuation of Ser. No. 58,451, Jun. 5, 1987, abandoned, which is a division of Ser. No. 604,702, Apr. 27, 1984, Pat. No. 4,711,574.

[51] Int. Cl.$^5$ .............................................. G01B 9/02
[52] U.S. Cl. .................................... 356/351; 356/349; 356/358
[58] Field of Search ............... 356/349, 351, 358, 361, 356/363

[56] References Cited

U.S. PATENT DOCUMENTS

| 2,568,589 | 9/1951 | Labhart | 356/361 |
| 3,788,746 | 1/1974 | Baldwin et al. | 356/106 |
| 3,976,379 | 8/1976 | Morokuma | 356/351 |

OTHER PUBLICATIONS

Roberts "Absolute Dilatometry Using a Polarization Interferometer: II" *J. Phys E:Sci. Instru.*, vol. 14, No. 12, pp. 1386–8, 12/81.

Gardner, Deane A., "Automatic Compensation", Hewlett–Packard Journal, Apr. 1983, p. 12.

Tanimura, Y., "A New Differential Laser Interferometer with a Multiplied Opitcal Path Difference", Annals of the CIRP, vol. 32/1/1983, p. 449 through 452.

Berthold, J. W., III, Jacobs, S. F. and Norton, M. A., "Dimensional Stability of Fused Solica, Invar, and Several Ultralow Thermal Expansion Materials", Applied Optics/vol. 15, No. 8, Aug. 1976, pp. 1898 Through 1899.

Bennett, S. J., "A Double-Passed Michelson Interferometer, Optics Communications", vol. 4, No. 6, Feb./Mar. 1972, pp. 428 Through 429.

Bouricius, G. M. B. and Clifford, S. F., "An Optical Interferometer Using Polarization Coating to Obtain Quadrature Phase Components", Review of Scientific Instruments, vol. 41, No. 12, Dec. 1970.

*Primary Examiner*—Davis L. Willis
*Assistant Examiner*—Matthew W. Koren

[57] ABSTRACT

An interferometer in which an input beam is divided into two beams, the first of which is incident on a movable first reflecting surface before being recombined in an output beam with the second of the beams. The path for each beam is selected to be as similar as possible to the path for the other beam so that small rotations or translations of elements used to direct the beams affect both beams equally and so that changes in the ambient conditions affect both beams equally. The two beams are directed by reflecting elements, each of which reflects both beams an equal number of times so that small rotations of the elements affect both beams equally. The second beam is incident on a second reflecting surface near the first surface so that the deadpath between the first and second surfaces is as small as possible without interfering with the motion of the first surface. When used as a dilatometer, the first surface is the surface of a specimen and the second surface is the surface of a platen to which the specimen is attached. In this case, the deadpath between the two surfaces is the length of the specimen and therefore is inherently minimized. An etalon can also be combined with the interferometer to enable the detection of the change in the index of refraction of a fluid in the etalon as a function of fluid physical parameters.

17 Claims, 9 Drawing Sheets

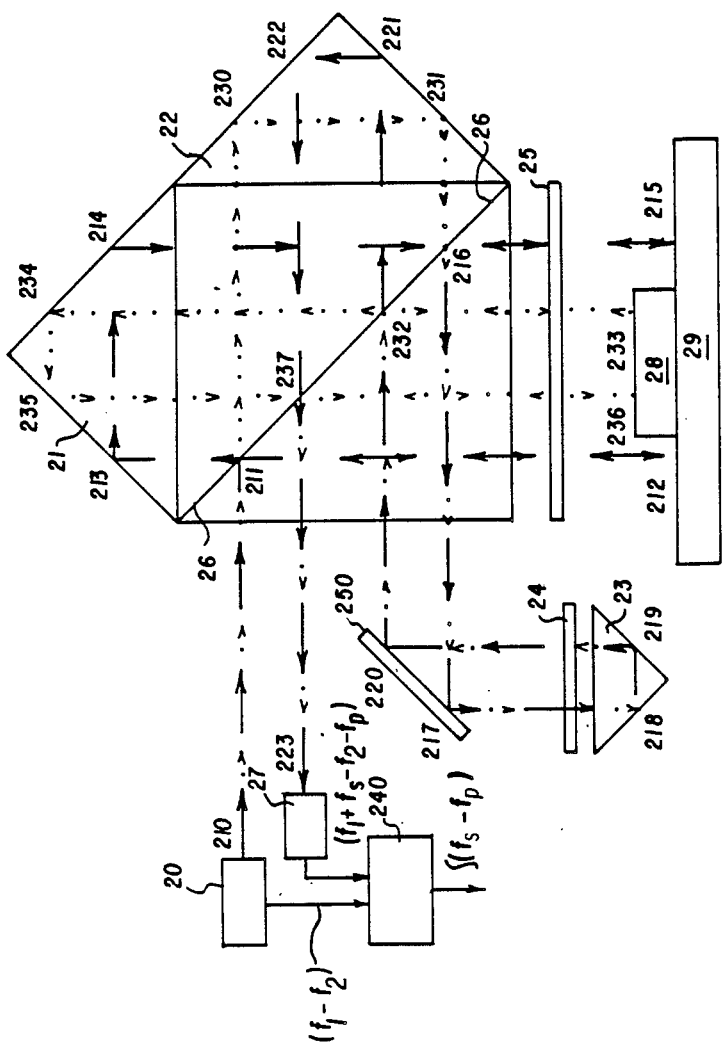

MINIMUM DEADPATH INTERFEROMETER AND DILATOMETER

CROSS REFERENCE TO RELATED APPLICATION

This application is a continuation of application Ser. No. 058,451, filed June 5, 1987, now abandoned, which is a division of application Ser. No. 604,702 filed 4/27/84 now U.S. Pat. No. 4,711,574.

BACKGROUND OF THE INVENTION

In the following discussion, the leading digits of a reference numeral indicate the first figure in which a particular element is presented. The invention relates generally to interferometry and more particularly to dilatometry. A dilatometer is utilized to measure the thermal coefficient of expansion of a specimen. In an optical dilatometer, interference effects are utilized to accurately measure the thermal variation of a linear dimension of the specimen.

In the dilatometer shown in FIG. 8 and presented by S. J. Bennet in the article "A Double-Passed Michelson Interferometer", Optics Communications, Vol. 4, Number 6 (Feb/Mar 1972), an incident light beam 81 is split by an input beam splitter 82 into a first light beam 83 and a second light beam 84. A polarizing beam splitter 85, an optical cube-corner 86 and a quarter wave plate 87 direct the first light beam twice from the surface of a platen 88 to which the specimen 89 has been attached. The optical paths involved in each reflection are parallel to each other and are located symmetrically with respect to a line normal to the surface. The second light beam is twice reflected in a similar manner from the surface of the specimen. The first and second light beams are combined by an output beam splitter 810 to produce an interference pattern in an output beam 811. As the temperature of the specimen is varied, the resulting change in the difference between the path lengths of the first light beam and the second light beam is proportional to the linear coefficient of thermal expansion of the specimen. The change in the interference resulting from the change in this path difference is detected to determine this coefficient. Since the distances involved are determined by detecting light that has been twice reflected from the surfaces of the specimen and the platen in the symmetrical manner described, the device is insensitive to translation or rotation. Only the linear expansion of the test object in the direction normal to the surface is detected so that the linear coefficient of expansion may be determined.

Unfortunately, in Bennet's device, the input and output beam splitters are glass parallelpipeds that are traversed by beam 84 but not by beam 83. As a result of this difference between the paths of beams 83 and 84, this device is sensitive to alignment between the input and output beam splitters and is also sensitive to thermal effects on these beam splitters such as thermal expansion and thermal variation of the index of refraction. Since the operation of the dilatometer requires heating or cooling of the specimen, often to extreme temperatures, it is desirable that the optical portion of the device be as insensitive to temperature as possible. For accurate fringe detection, the wavefronts of the emergent light beams must be substantially parallel or else undesired interference across the cross-section of the combined output light beams will result which degrades detection of the desired interference between the combined output light beams. The requirement that the output light beams be parallel requires that the input and output beam splitters be aligned within very strict tolerances (on the order of 10 arcseconds as suggested in the Bennet article). To manufacture and maintain these tolerances is both difficult and expensive.

A dilatometer that eliminates this stringent alignment problem is shown in FIG. 9 and is presented in U.S. Pat. No. 3,788,746 entitled OPTICAL DILATOMETER issued to Richard R. Baldwin and Bruce J. Ruff on Jan. 29, 1974. In that dilatometer, an input beam 91 is divided by an input beam splitter 92 and a beam bender 93 into a first input beam 94 and a second input beam 95. Each input beam has two perpendicularly polarized components that are separately directed by a polarizing beam splitter 96 and a pair of cube corners 97 and 98. The first component of each of beams 94 and 95 passes through beam splitter 96 to cube corner 98 and back out to a pair of detectors 912 and 913, respectively. The second component of each of beams 94 and 95 is directed by polarizing beam splitter 96, cube corner 97 and quarter wave plate 99 to reflect twice off of specimen 911 and platen 910, respectively, in a symmetrical manner as in the article by Bennet and then to pass on into detectors 912 and 913, respectively. Each of these second components interferes with its associated first component. Because neither of the two first components impinges on the platen or the specimen, each of these first components serves to produce a reference path length against which the path length of its associated second component is compared. The outputs of the detectors are compared to determine the linear coefficient of thermal expansion for the specimen.

Although this dilatometer does not require that the input beam splitter 92 by precisely aligned with another beam splitter, as is required to avoid unwanted interference effects in the dilatometer presented by Bennet, there must be a reasonable degree of alignment between input beam splitter 92 and beam bender 93 or else the second component of beam 94 will overlap onto the platen or the second component of beam 95 will overlap onto the specimen. This problem becomes increasingly important with increased distance between the dilatometer and the specimen/platen combination. In addition, the use of two detectors increases the cost and complexity of this dilatometer. Also, the first component of each of beams 94 and 95 reflects off of cube corner 98 but not off of cube corner 97 whereas the second component of each of beams 94 and 95 reflects off of cube corner 97 but not off of cube corner 98. Therefore, cube corner 97 must be precisely aligned with cube corner 98 or else similar undesired interference problems can arise. Misalignment of a cube corner will not affect the direction of either of the components in the output beam, but it can produce a lateral displacement between these two components, thereby affecting the interference effects observed in the output beam. It would be preferable to have a device in which interfering beams passed through all elements of the device in a manner which made the device insensitive to independent small rotations and translations of all of its elements.

SUMMARY OF THE INVENTION

In accordance with the illustrated preferred embodiment, an interferometer and dilatometer are presented which are insensitive to small amounts of misalignment of their component parts. The path of each of a pair of interfering light beams are closely spaced and are of nearly equal length so that effects due to ambient conditions such as variations in the index of refraction of the ambient atmosphere will affect both beams comparably, thereby substantially eliminating undesired effects due to the ambient conditions. The dilatometer is a special case of the interferometer and therefore much of the discussion about the dilatometer is equally applicable to the interferometer.

The interferometer utilizes a polarizing beam splitter that transmits a first polarization of light and reflects a second polarization of light. An incident beam containing a first component having the first polarization and a second component having the second polarization is incident on the polarizing beam splitter. A first, second and third cube corners are utilized to fold light beams incident on them from the polarizing beam splitter back tot he polarizing beam splitter. This return path in each case is parallel to the path incident from the polarizing beam splitter. A pair of quarter wave plates are utilized to convert one polarization into the other polarization thereby converting a beam from a state in which it would be transmitted (reflected) by the polarizing beam splitter into a state in which it would be reflected (transmitted). The two polarizations are recombined in an output beam in which the interference between the two components is detected by a detector. The optical elements, including the polarizing beam splitter, cube corners and quarter wave plates are arranged so that every element reflecting one component of the input light beam also reflects the other component an equal number of times so that small misalignment effects show up equally in both beams and thereby do not affect the interference produced in the output beam. The term "common mode" will be used herein to describe those elements of the interferometer in which the optical paths of both components are equal, in which both components are reflected an equal number of times and in which any misalignment of that element shows up substantially equally in both components. "Common mode" will also be used to refer to those portions of the optical path of one beam that are closely spaced and of equal length so that ambient effects will affect both components substantially equally. The "optical path length" for a beam is the integral along the path of the local index of refraction of the medium through which the beam is travelling. For the interferometer to be insensitive to misalignment and ambient effects, the difference in the optical path lengths of the two components must be insensitive to misalignment and ambient effects. The portion of such optical paths that is not common mode will be referred to herein as the "deadpath". The interferometer design is selected to minimize the deadpath.

First and second planar reflecting surfaces are also included to reflect the light beams. In the case of a dilatometer, the first and second planar reflecting surfaces are the front surfaces of a specimen and a platen, respectively. Although the specimen is typically attached to the platen so that the first surface is not freely movable with respect to the second surface, both surfaces will be referred to herein as movable surfaces because it is the motion of one relative to the other that is to be measured. The first component of the input light beam is incident on the first planar reflecting surface at least once and the second component of the input light beam is incident on the second planar reflecting surface at least once. The number of times that the first component is incident on the first reflecting surface is not equal to the number of times that the second component is incident on that surface so that relative translation of the first reflecting surface in the direction normal to that surface will change the relative length of the path of the first component compared to the length of the path of the second component. This makes the interferometer sensitive to such relative motion between the first plane reflecting surface and the second reflecting surface.

It can be advantageous to have one of the components incident on a given surface more than once. For example, in the dilatometer by Bennet presented above, the symmetrical manner in which the light beams are twice reflected off of the platen and the specimen enables the interference effects in the output beam to be insensitive to translations and rotations of the specimen/platen pair. As pointed out in the reference Y. Tanimura, "A New Differential Laser Interferometer with a Multiplied Optical Path Difference", Annals of the CIRP, Vol. 32/1/1983, page 449, the sensitivity of an interferometer can be increased by multiple reflections off of the surfaces whose relative movement is to be determined.

If a component of the input beam is incident more than once along parallel paths onto one of the planar reflecting surfaces, then the spacing of the beams can be arranged to make the total path length for that component independent of small rotations about a selected point in the surface of that planar reflecting surface. A centroid can be defined for the set of points where these multiple incidences occur on that reflecting surface. The centroid has the property that for small rotations about that point the cumulative change in the path length of the component incident on that surface is unchanged. Therefore, the beam arrangement is chosen to make the centroid coincide with the selected point.

The concept of the centroid is illustrated in FIG. 10. In that figure, one of the components is shown incident four times on a specimen 101 and platen 102. This incidence is represented by the set of beams 105–108. The first and second reflecting surfaces are the surfaces 103 and 104 of the specimen and platen, respectively. The set of points used to define the centroid are the intersections 109, 1010, 1011 and 1012 of the beams 105–108 with an imaginary plane 1013 coplanar with surface 103. Point 1014 is the centroid of these intersection points.

In the case of a dilatometer, the first and second specimen/platen pair are rotated about centroid 1014 (as illustrated by the dotted outline of the specimen and platen), then some of the paths for beams 105–108 are lengthened (e.g., by lengths A and B) and some are shortened (e.g., by lengths C and D), but the sum of the changes in the path length of that component is zero. The centroid for the points of incidence of the other component on plane 1013 should be selected to coincide with the centroid shown in FIG. 10 so that a rotation about the centroid will not affect the interference effects in the output beam. The set of beams for one component includes the set of all beams for that component striking either of these reflecting surfaces.

The number of reflections of the first component from either planar reflecting surface is equal to the number of reflections of the second component from either planar reflecting surface so that translations of the specimen/platen pair in the direction of the normal to the planar reflecting surfaces does not affect the interference pattern in the output light beam. If the interferometer is insensitive to all small rotations of the specimen/platen combination around the centroid and is furthermore insensitive to all translations of the specimen/platen combination, then the interferometer is insensitive to small rotations of the specimen/platen combination around any point.

The use of the pair of planar reflecting surfaces also makes the interferometer suitable for use in photolithography equipment. The first of the planar reflecting surfaces is mounted on a side of a movable stage the position of which is to be detected. The second planar reflecting surface is mounted in a fixed reference position which does not move with the stage. In an alternative embodiment, one of the cube corners in the interferometer is replaced with a set of three turning mirrors and a second pair of planar reflecting surfaces mounted on the movable stage. Additional reference reflectors are symmetrically mounted on either side of the stage. The paths for both components are kept close together and of comparable length so that ambient conditions affect both components substantially equally so that there is substantially no ambient effect in the resultant interference pattern in the output beam. The portion of the beam paths which is not common mode is kept to a minimum. In addition, the total paths are selected to be equal for the two beams when the stage is centered between the two planar reflecting surfaces.

The interferometer can also be used to measure the change in the index of refraction of a fluid with changes in fluid parameters. In this application, the planar reflecting surfaces are the outside front face of an etalon and the inside back face of the etalon. The etalon is formed of a dimensionally stable material so that its length remains constant while the fluid parameters are varied. Any resulting shift in the interference pattern is therefore due to a change in the index of refraction of the fluid.

DESCRIPTION OF THE FIGURES

FIG. 2 is an alternative embodiment of the dilatometer.

3A-3C illustrate an embodiment in which the light beams are not all coplanar.

Figure 4:
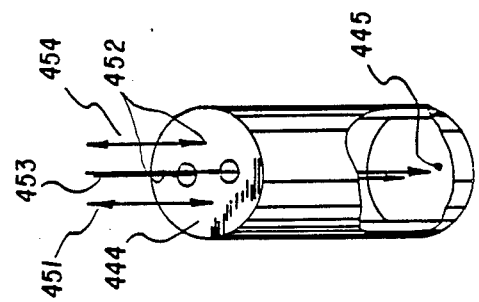

FIG. 4 shows an etalon suitable for use with the interferometer to measure variations in the index of refraction of a fluid.

Figure 5:
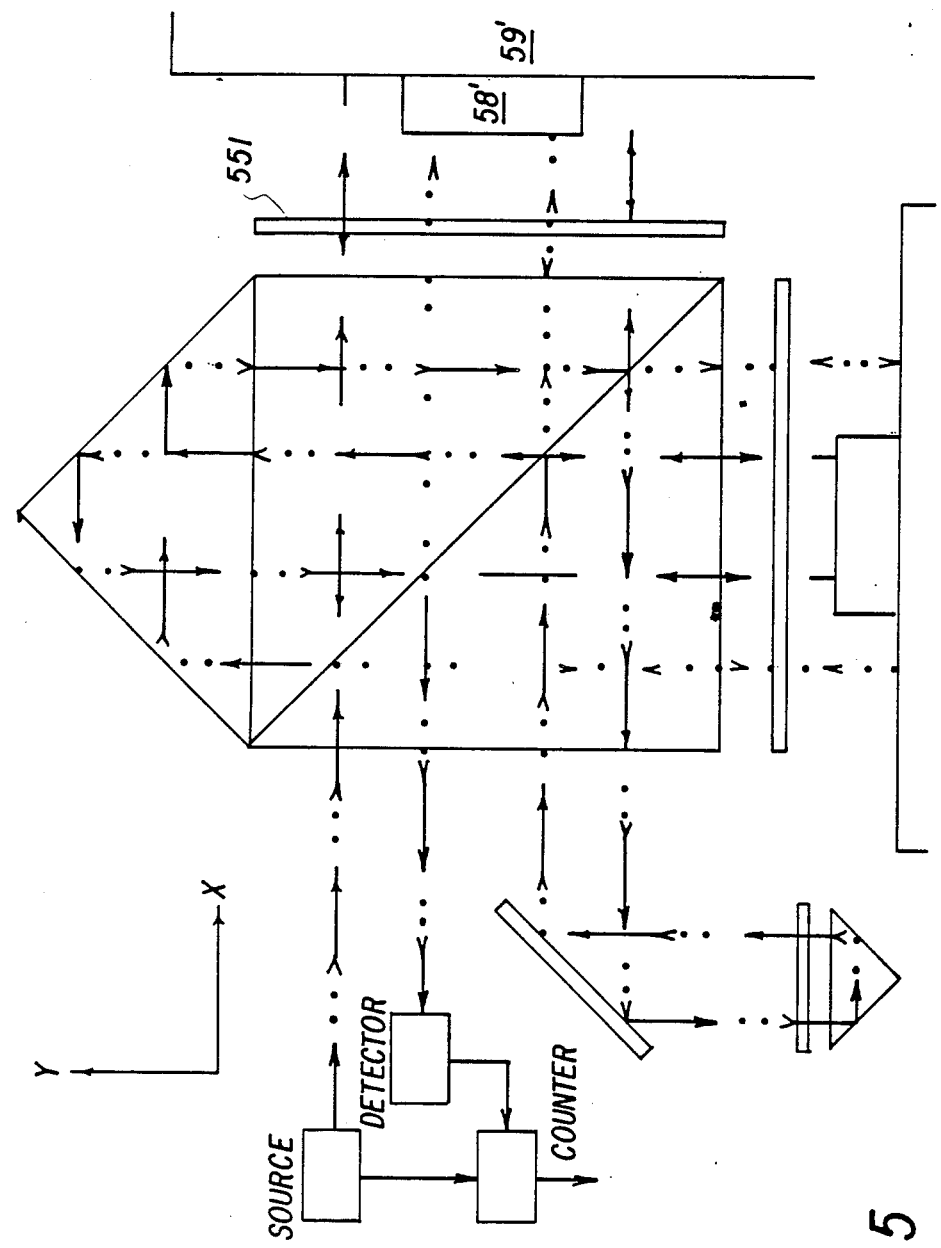

FIG. 5 is a block diagram of an embodiment of the interferometer in which the relative displacement between a set of four reflecting surfaces is detected.

Figure 6:
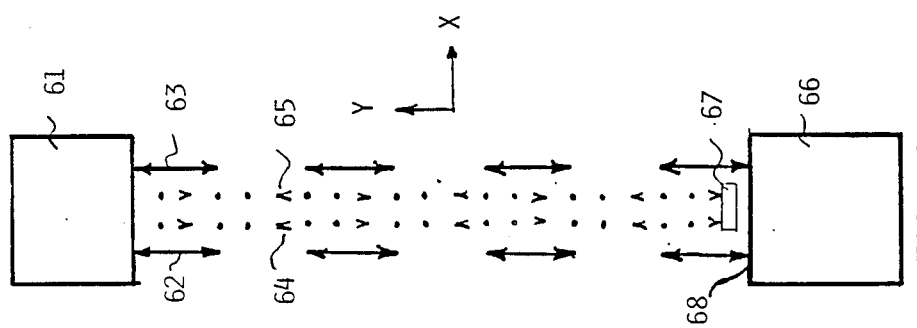

FIG. 6 illustrates the use of the interferometer in detecting motion of a movable stage in photolithography equipment.

Figure 7:
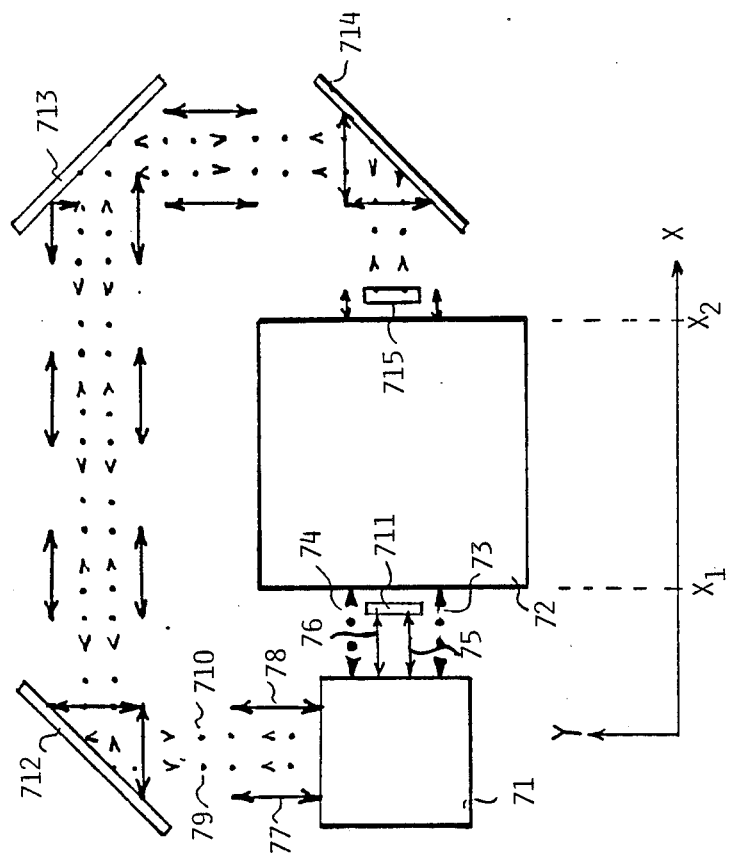

FIG. 7 illustrates an alternative embodiment of the use of the interferometer in detecting motion of a movable stage in photolithography equipment.

Figure 8:
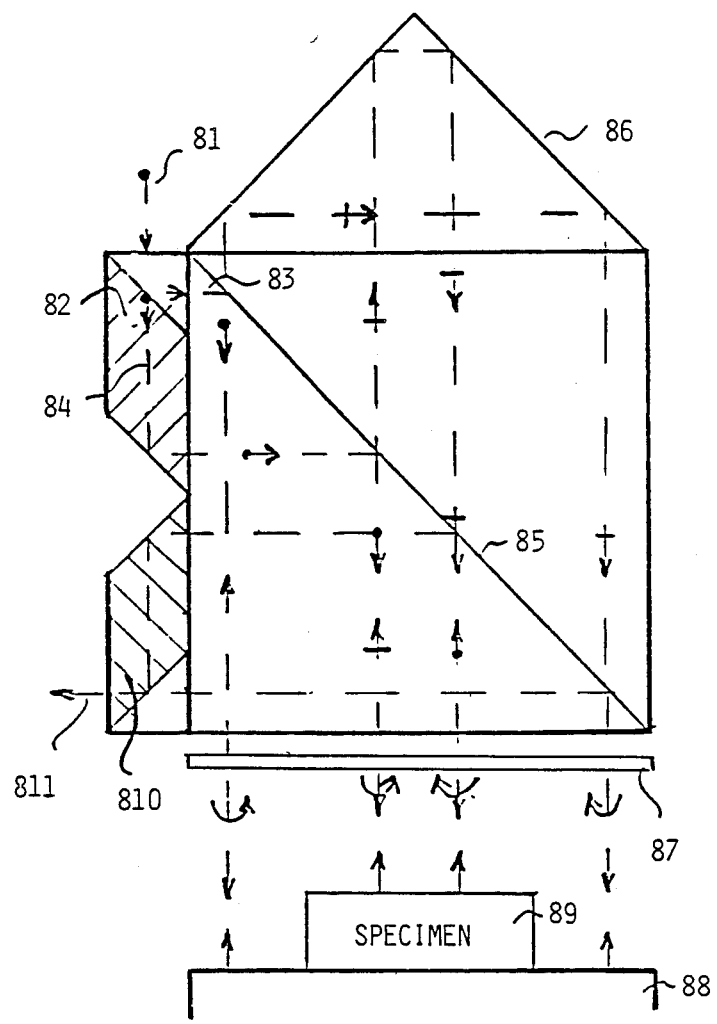

FIG. 8 shows a dilatometer presented in a article by S. J. Bennet.

Figure 9:
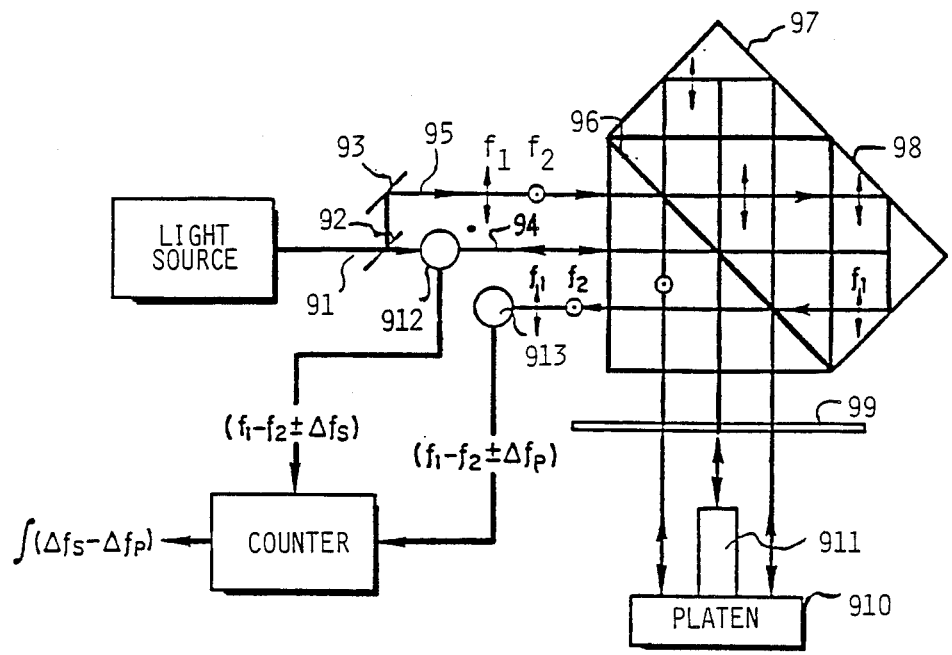

FIG. 9 shows a dilatometer presented in U.S. Pat. No. 3,788,746.

Figure 10:
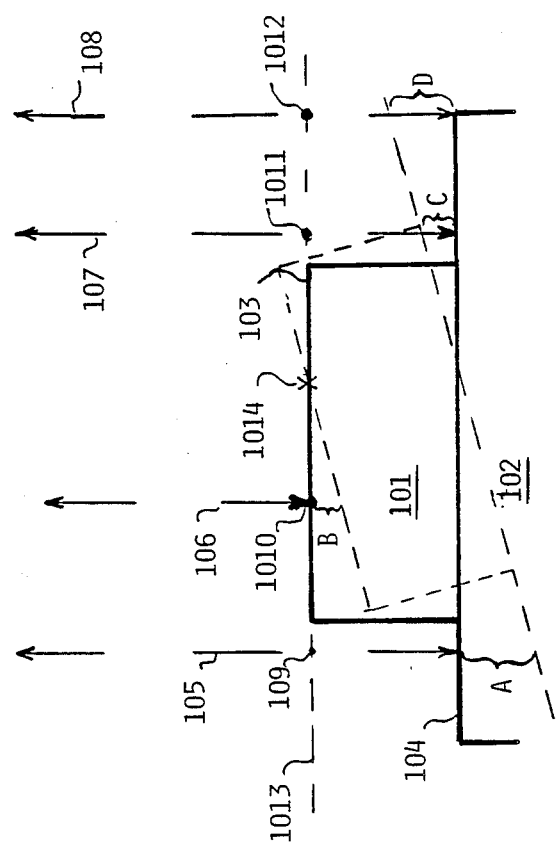

FIG. 10 illustrates the concept of centroid for a component incident on a surface a plurality of times.

DESCRIPTION OF THE PREFERRED EMBODIMENT

Figure 1:
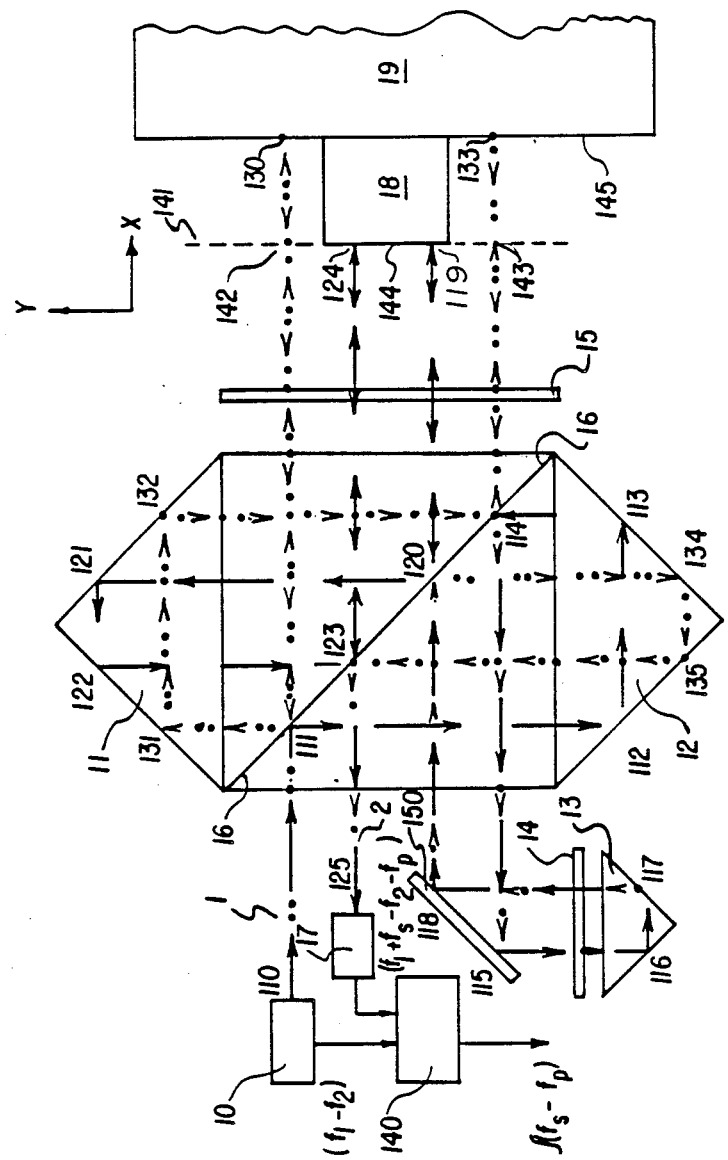
FIG. 1 is a block diagram of a dilatometer having minimum deadpath.

In FIG. 1 is shown a dilatometer in which the deadpath is minimal so that the device is insensitive to small misalignment of its component parts and is also insensitive to changes in the ambient conditions. A light beam 1 containing a first component having a first polarization and a second component having a second polarization is produced by a light source 10. Although polychromatic light can be used, it is preferred that each component be monochromatic so that interference effects occur over large optical path differences such as would result when a long specimen is tested. A set of three folding elements such as cube corners 11-13 are each utilized to fold an incident optical path back along a path parallel to the incident beam. A pair of quarter wave plates 14 and 15 are each used to convert a beam of one polarization into the other polarization. A polarizing beam splitter 16 is utilized to reflect a component having the first polarization and to transmit a component having the second polarization. In one particular choice, the polarizations are chosen to be linearly polarized at ninety degrees to one another. Both components are recombined to form an output beam 2 in which the two components interfere. Because the two components are orthogonal, they do not interfere in the traditional sense in which constructive and destructive interference occurs. Instead, the two components add vectorially as orthogonal components. The polarization of the resulting vector is dependent on the relative optical path lengths of the two components and such dependence will be referred to herein as interference. The output beam enters a detector which measures the interference effects between the two light beams. For the case in which both components have the same frequency, a suitable detector is shown in the article by G. M. B. Bouricius and S. F. Clifford entitled "An optical interferometer using polarization coating to obtain quadrature phase components" and published in *Review of Scientific Instruments*, Vol. 41, No. 12, Dec, 1970. For the case in which the two components have different frequencies, a suitable detector is shown in the reference by Bagley discussed in the Background.

The elements 11-16 direct the two components so that the first component is incident on a specimen 18 at two points of incidence 119 and 124 and the second component is incident on a platen 19 at two points of incidence 130 and 133. The surface of the specimen on which the first component is incident serves as a first planar reflecting surface 144 and the surface of the platen on which the second component is incident serves as a second planar reflecting surface 145. The second component crosses an imaginary plane 141 (which is coplanar with surface 144) at points 142 and 143. The centroid of points 142 and 143 is equal to the centroid of points 119 and 124 so that the interference effects in output beam 2 are insensitive to small rotations of the specimen/platen pair about these centroids. Surfaces 144 and 145 are parallel so that these interference effects are also insensitive to the translation of the specimen/platen pair in a direction perpendicular to the normal to these surfaces. The interference effects are affected only by motion of surface 144 relative to surface 145 in the direction of this surface normal. Therefore, the expansion or contraction of the specimen in the direction of this surface normal is detected by the dilatometer.

In one particular embodiment, the first component has frequency $f_1$, the second component has frequency $f_2$ and detector 17 includes a mixing polarizer and a photoelectric detector in a well known manner (see for example FIG. 2 in U.S. Pat. No. 3,458,259 by A. S.

Bagley et al). This produces a detector output signal at frequency $f_1+f_s-f_2-f_p$ where $f_s$ is the Doppler shift in frequency of the first component due to motion of the specimen and $f_p$ is the Doppler shift in frequency of the second component due to motion of the platen. This output signal and an output signal of frequency $f_1-f_2$ from source 10 are fed to an integrator such as electronic reversible counter 140 which integrates the difference between the frequencies of those signals. The output of counter 140 is thus proportional to the accumulated difference in displacements between the surface of the specimen and the surface of the platen. A knowledge of the temperature change undergone by the sample then allows a simple calculation of the linear coefficient of expansion of the specimen. For another choice of detection, the two components need not have different frequencies.

The elements 11-16 combine to direct the first component along the path shown by solid arrows and the second component along the dotted path. The second component travels from point 110 on source 10 to point 111 on polarizing beam splitter 16 where it is transmitted on to point 130 on second reflecting surface 145. In its passage to point 130 and back to point 111, the second component passes twice through quarter wave plate 15 so that its polarization is converted to the first polarization. Because of this, the second component is reflected at point 111 to cube corner 11 where it is further reflected at points 131 and 132 to point 114 on polarizing beam splitter 16. This beam is still has the first polarization and therefore it is reflected at point 114 to point 133 where it is further reflected back through point 114 to point 115 on a beam turning element such as mirror 150. Further reflections at points 116, 117, 118, 120, 134, 135, and 123 then direct the beam into detector 17 at point 125. In a similar manner, the first component is directed by elements 11-16 and 150 along the path which sequentially passes through points 110-125. It should be noted that every one of these elements reflects the first component as many times as it reflects the second component. More particularly, the polarizing beam splitter, which has two surfaces which can each selectively reflect incident light beams depending on the polarization of the light beams, reflects each of the two components an equal number of times from both sides. This makes the interference effects in the output beam insensitive to small translations of each of these element. In addition, the optical paths of the two interfering components are equal in elements 11-16 and identical in elements 13, 14, and 15. This means that, unlike Bennett, the device is not sensitive to the temperature of these elements. In addition, the centroids of the points of incidence of the first component on each of the elements 11-16 and 150 coincide with the centroids for each of those elements of the second component. This makes the interference effects in the output beam insensitive to small rotations of each of these elements about its associated centroid. Therefore, this dilatometer is insensitive to small amounts of misalignment arising during manufacture, aging or short term effects due to changes in the ambient conditions.

In FIG. 2 is shown an alternative embodiment in which elements 21-26 and 250 cooperate in a manner analogous to elements 11-16 and 150 in FIG. 1. The first component is directed along the optical path which successively passes through points 210-223. In an analogous manner, the second component can be easily traced through this embodiment. This embodiment likewise has the above-described properties that make it insensitive to small translations and rotations of each of its elements.

Figure 3A:
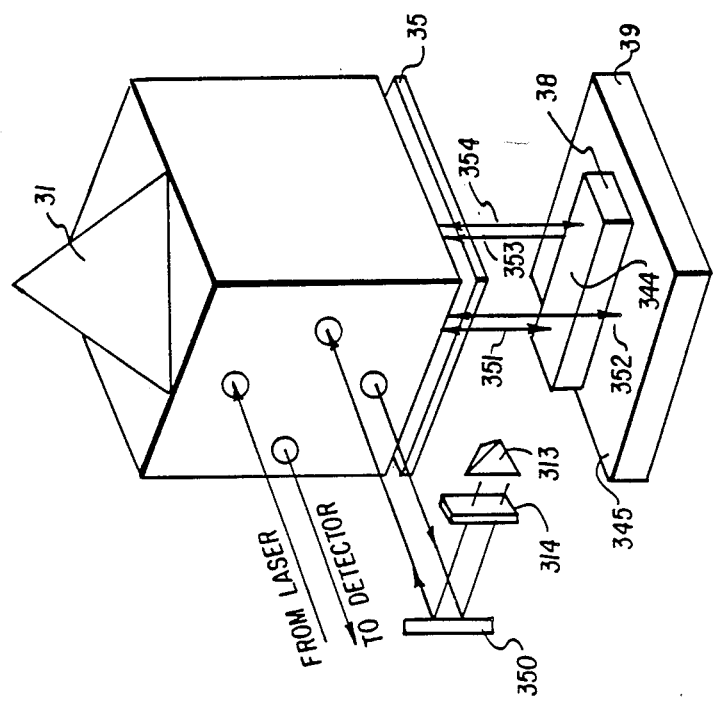
Figure 3B:
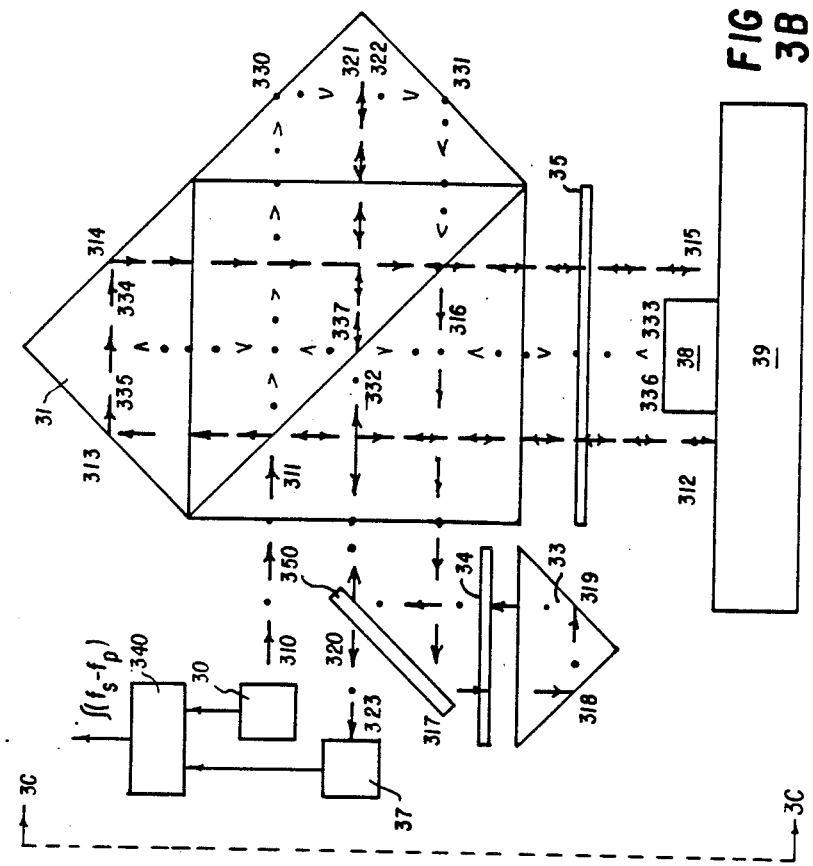
Figure 3C:
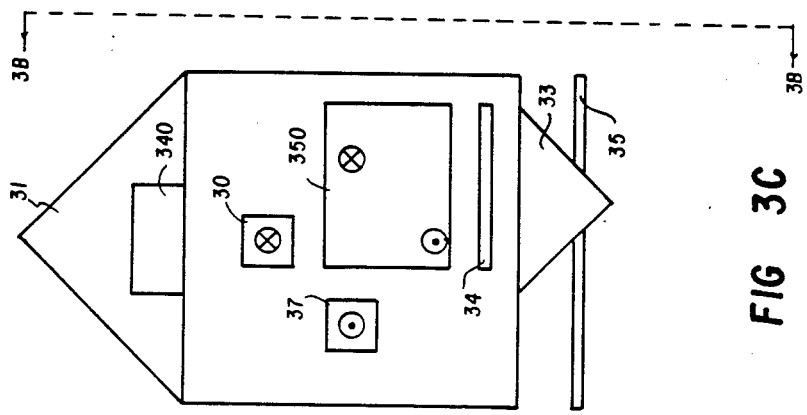

The embodiments presented in FIGS. 1 and 2 are essentially two dimensional in that all of the light paths lie in a two dimensional plane. In FIGS. 3A-3C is shown an embodiment in which the light beams are not all coplanar. Each element in FIGS. 3A-3C designated as 3x or 3yz serves the same purpose as its counter part 2x or 2yz in FIG. 2 and therefore the operation of the embodiment in FIG. 3 is easily understood by reference to the operation of the embodiment in FIG. 2.

In FIG. 4 is shown an etalon which is suitable for use with the dilatometer to measure the change of the index of refraction of a fluid contained in the etalon. The etalon is made of a material that is dimensionally stable under a change in ambient conditions. In particular, if the thermal variation of the index of refraction of a fluid is to be determined, then the interior of the etalon is filled with the fluid and the material chosen for the etalon must have a substantially zero linear coefficient of thermal expansion. A useful choice for the etalon is Zerodur produced by Heraus-Schott (see the paper entitled "Dimensional stability of fused silica, Invar and several ultralow thermal expansion materials" written by J. W. Berthold III, et al and published in August 1976 in volume 15, No. 8 of APPLIED OPTICS). The etalon replaces specimen 38 and platen 39 in FIG. 3A. Each of the elements 4xy in FIG. 4 performs the same function as its counterpart 3xy in FIG. 3A. In particular, the outer front face of the etalon serves as the first planar reflective surface 444 and the inner back face of the etalon serves as the second planar reflective surface 445.

In FIG. 5 is shown an embodiment similar to that in FIG. 2, but in which a cube corner has been replaced by a quarter wave plate 551, a second specimen 58' and a second platen 59'. The interference pattern is responsive to the relative motion of specimen 58 relative to platen 59 in the positive y-direction minus the relative motion of specimen 58' relative to platen 59' in the negative x-direction. This embodiment of the interferometer is useful in photolithography equipment as illustrated in FIG. 7.

It should be noticed that in each of these embodiments, the cube corners analogous to cube corner 13 and the quarter wave plates analogous to quarter wave plate 14 in FIG. 1 serve the same role as in FIG. 1. Namely, in FIG. 1, cube corner 13 functions as a retroreflector which bends the light paths incident on it from the polarizing beam splitter 16 back to the polarizing beam splitter In each of these cases, the beam incident on the cube corner is bent into a direction antiparallel to the incident beam and displaced laterally from the incident beam. Quarter wave plate 14 functions as a polarization interchanger which converts the polarization of a beam incident on cube corner 13 into the conjugate polarization so that if it was transmitted (reflected) by the polarizing beam splitter on its last incidence on it, then on its next incidence on it, the beam will be reflected (transmitted). This causes each component after incidence on elements 13 and 14 to traverse a path which is parallel to the path traversed by the other component prior to incidence on elements 13 and 14. This results in both components reflecting an equal number of times off of all of the optical elements other than the first and second reflecting surfaces, thereby making the interferometer insensitive to small misalignments of its component parts.

The interferometer of FIG. 1 can be utilized to detect the motion of a wafer stage in lithography equipment as is illustrated in FIG. 6. In that figure, the interferometer produces a first component which travels along parallel paths 62 and 63 to a first planar reflecting surface 68 mounted on the side of a wafer stage 66. The points of incidence on surface 68 are analogous to points 130 and 133 in FIG. 1. The interferometer also produces a second component which travels along a pair of parallel paths 64 and 65 to and from a second planar reflecting element 67 which does not move with the wafer stage. The interferometer measures the motion in the y-direction of wafer stage 66 relative to second planar reflecting surface 67. Because reflecting elements 67 and 68 are planar, the wafer stage can also be moved in the x-direction without interfering with measurement of motion in the y-direction. A similar arrangement can be used to measure this x-direction motion.

Because of the high degree of accuracy with which the wafer stage needs to be moved in current state of the art lithography equipment, thermal expansion variation of the wafer stage dimensions can produce spurious apparent motion of wafer stage 66. In FIG. 7 is an embodiment in which this spurious motion is removed. In that embodiment an interferometer 71 measures the x-direction motion of stage 72. The interferometer produces a first component along parallel paths 73 and 74 to a first reflecting surface on stage 72. It also produces a second component along parallel paths 75 and 76 to a second planar reflecting surface 711 which does not move with the stage. Similarly, the first component travels along a pair of parallel paths 77 and 78 and the second component travels along a pair of parallel paths 79 and 710 to wafer stage 72 and planar reflecting element 715, respectively. Turning elements such as mirrors 712-713 respectively direct these beams onto stage 72 and element 715 along a direction normal to both of them. This interferometer measures the sum $x_1 + x_2$ and therefore it is responsive to x-direction translation of the stage, but is not responsive to expansion of the stage in the x-direction. Paths 79 and 710 are kept in close proximity to paths 77 and 78 so that they are common mode except for the portion of paths 77 and 78 between the right edge of stage 72 the reflecting surface of element 715. This distance is kept to a minimum to minimize the deadpath in the system. In general, the use of two pairs of adjacent parallel paths as in the interferometer and dilatometer enables the deadpath to be minimized by locating the first planar reflecting element near the second planar reflecting element even though the remainder of the interferometer is distant from those elements. This enables the deadpath to be minimized even in situations in which it is inconvenient to locate the interferometer near the element whose motion is to be measured. The deadpath should be as small as possible without restricting the range of motion of the wafer stage.

I claim:

1. A minimum deadpath interferometer for measuring the change in optical path length of an optical beam between a sample plane and a reference plane, said interferometer comprising:
   a first reflecting surface coplanar with the sample plane;
   a second reflecting surface coplanar with the reference plane; and
   optical means having a plurality of elements including a polarizing beam splitter for transmitting a beam of a first polarization and reflecting a beam of a second polarization,
   for producing a first optical beam and a second optical beam from light supplied from a light source, said first and second beams being directed along paths that are common mode except for the portion of their paths between the sample and reference planes;
   for directing the first beam along a first beam path that reflects off of said first reflecting surface;
   for directing the second beam along a second beam path that reflect off of said second reflecting surface;
   for directing said reflected first and second beams into an output beam in which the first and second beams overlap and in which the first and second beams are substantially parallel, such parallelism being substantially independent of small rotations of the first reflecting surface, of the second reflecting surface and of the elements of the optical means.

2. An interferometer as in claim 1 wherein, except for a portion of the first beam path between the sample and reference planes, the first and second beam paths can each be broken up into segments, each segment of one of these paths being associated with an equal length segment of the other path, said associated segments being close enough to one another that ambient effects on one segment are substantially equal to ambient effects on its associated segment, whereby the interference effects in the output beam are substantially independent of ambient conditions over the common mode part of the paths of the first and second light beams.

3. An interferometer as in claim 1 wherein any element of the optical means which reflects one of the first and second beams of light also reflects the other of these two beams the same number of times, whereby a small rotation of one of these elements introduces the same amount of angular change into the direction of the first beam at that element as is introduced into the second beam at that element.

4. An interferometer as in claim 3 wherein the optical means comprises:
   a polarizing beam splitter having two faces each of which transmits incident light having a first polarization and reflects incident light having a second polarization;
   said beam splitter dividing incident light from said light source into the first and second beams; and
   first beam directing means for directing each of the first and second beams to reflect off of the polarizing beam splitter the same number of times as the other beam.

5. An interferometer as in claim 4 wherein each of the first and second beams reflects off of each face of the polarizing beam splitter the same number of times.

6. An interferometer as in claim 1 further comprising an etalon which contains a fluid, the change in the index of refraction of which is to be determined as a function of the controlled change in physical parameters of the fluid, said etalon having a first face whose outside surface is the first reflecting surface, having a second face, parallel to the first face, whose inside surface is the second reflecting surface and being formed of a material which is dimensionally stable to change in the fluid parameters that are varied.

7. An interferometer as in claim 1 wherein the first and second reflecting surfaces are planar and parallel to one another, whereby the movable first reflecting surface can be translated in a direction perpendicular to the normal to these two surfaces without affecting the interference effects in the output beam.

8. An interferometer as in claim 7 wherein the first reflecting element is a planar surface of a specimen and the second reflecting element is a planar surface of a platen to which the specimen is attached, thereby forming a specimen/platen combination and wherein the first and second paths are each incident on the specimen/platen combination a plurality of times such that the points of incidence on the specimen and the points of incidence on the platen separately have centroids that coincide, whereby the difference in the optical path lengths between the first and second paths is insensitive to small rotations and translations of the specimen/platen combination.

9. An interferometer as in claim 1 wherein said optical means includes a first retroreflector that reflects the first beam, after a first reflection off of the first reflecting surface, back to the first reflecting surface for a second reflection, said first beam travelling along anti-parallel paths to said first retroreflector and back to the said first reflecting surface, whereby the direction of the first beam after this second reflection is independent of small rotations of the first reflecting surface.

10. An interferometer as in claim 9 wherein said optical means includes a second retroreflector that reflects the second beam, after a first reflection off of the second reflecting surface, back to the second reflecting surface for a second reflection, said second beam travelling along anti-parallel paths to said second retroreflector and back to the said second reflecting surface, whereby the direction of the second beam after this second reflection is independent of small rotations of the second reflecting surface.

11. An interferometer as in claim 10 wherein said optical means comprises:
a polarizing beam splitter that splits a beam of light from said light source into a first beam having a first polarization that passes through the beam splitter and into a second beam having a second polarization that reflects off of the beam splitter, each of these two polarizations being referred to as conjugate to the other of these polarizations;
third, fourth and fifth retroreflectors that each retroreflects the first beam and the second beam back to the polarizing beam splitter;
first conversion means, located between the polarizing beam splitter and the first and second reflecting surfaces, for converting each beam incident on one of said reflecting surfaces into the conjugate polarization;
second conversion means, located between the polarizing beam splitter and the fifth retroreflector, for converting the polarization of each beam incident on said fifth retroreflector into the conjugate polarization;
said first beam being incident on the polarizing beam splitter, the third, fourth and fifth retroreflectors, the first and second conversion means and said first reflecting surface; and
said second beam being incident on the polarizing beam splitter, the third, fourth and fifth retroreflectors, the first and second conversion means and said second reflecting surface.

12. A minimum deadpath interferometer for measuring the change in optical path length of an optical beam between a sample plane and a reference plane, said interferometer comprising:
a first reflecting surface coplanar with the sample plane;
a second reflecting surface coplanar with the reference plane;
a polarizing beam splitter for transmitting a beam component of a first polarization and reflecting a beam component of a second polarization for splitting an incident light beam into a first component which reflects at least twice from the first reflecting surface, and a second component which reflects at least twice from the second reflecting surface at locations the centroid of which is at the same location as the centroid of the reflections of the first component from the first surface, and for recombining the reflected components into an output beam; and
three retroreflectors for folding component beams from the polarizing beam splitter back onto the polarizing beam splitter along a path parallel to and displaced from the path from the polarizing beam splitter and arranged so that the first and second components are each reflected the same number of times by each retroreflector and by each side of the beam splitter, and the path lengths of each component in each optical element being equal.

13. An interferometer as recited in claim 12 further comprising a polarization interchanger and beam bender between the polarizing beam splitter and one of the retroreflectors, and a polarization interchanger between the beam splitter and the first and second reflecting surfaces.

14. An interferometer as recited in claim 13 wherein the beam splitter is rectangular with a diagonal beam splitting plane, each retroreflector receives light from and returns light to a face of the beam splitter different from the other retroreflectors, and the reflecting surfaces are aligned with a fourth face of the beam splitter.

15. A minimum deadpath interferometer for measuring the change in optical path length on an optical beam between a sample plane and a reference plane, said interferometer comprising:
a first reflecting surface coplanar with the sample plane;
a second reflecting surface coplanar with the reference plane;
optical means having a plurality of elements including a polarizing beam splitter for transmitting a beam component of a first polarization and reflecting a beam component of a second polarization for splitting an incident light beam into a first component which reflects at least twice from the first reflecting surface, and a second component which reflects at least twice from the second reflecting surface at locations the centroid of which is at the same location as the centroid of the reflections of the first component from the first surface, and for recombining the reflected components into an output beam;
first and second retroreflectors for folding component beams from the polarizing beam splitter back onto the polarizing beam splitter along a path parallel to and displaced from the path from the polarizing beam splitter and arranged so that the first and second components are each reflected twice by each retroreflector and twice by each side of the beam splitter; and a third retroreflector for folding component beams from the polarizing beam splitter back onto the polarizing beam splitter along a path parallel to and displaced from the path from the polarizing beam splitter and arranged so that the first and second components are coincident through the third retroreflector.

16. An interferometer as recited in claim 15 further comprising a polarization interchanger and beam bender between the polarizing beam splitter and the third retroreflector, and a polarization interchanger between the beam splitter and the first and second reflecting surfaces.

17. An interferometer as recited in claim 16 wherein the beam splitter is rectangular with a diagonal beam splitting plane, each retroreflector receives light from and returns light to a face of the beam splitter different from the other retroreflectors, and the reflecting surfaces are aligned with a fourth face of the beam splitter.

* * * * *